US011584917B2

(12) United States Patent
Wieland

(10) Patent No.: US 11,584,917 B2
(45) Date of Patent: Feb. 21, 2023

(54) CHEMICALLY DEFINED MEDIUM FOR THE CULTURE OF CANCER STEM CELL (CSC) CONTAINING CELL POPULATIONS

(71) Applicant: PROMOCELL GMBH, Heidelberg (DE)

(72) Inventor: Hagen Wieland, Heidelberg (DE)

(73) Assignee: PROMOCELL GMBH, Heidelberg (DE)

( * ) Notice: Subject to any disclaimer, the term of this patent is extended or adjusted under 35 U.S.C. 154(b) by 718 days.

(21) Appl. No.: 15/998,586

(22) PCT Filed: Feb. 17, 2017

(86) PCT No.: PCT/EP2017/053666
§ 371 (c)(1),
(2) Date: Aug. 16, 2018

(87) PCT Pub. No.: WO2017/140876
PCT Pub. Date: Aug. 24, 2017

(65) Prior Publication Data
US 2019/0153396 A1 May 23, 2019

(30) Foreign Application Priority Data
Feb. 17, 2016 (EP) .................................. 16156163

(51) Int. Cl.
*C12N 5/00* (2006.01)
*C12N 5/09* (2010.01)
(Continued)

(52) U.S. Cl.
CPC ......... *C12N 5/0693* (2013.01); *C12N 5/0062* (2013.01); *C12N 5/0695* (2013.01);
(Continued)

(58) Field of Classification Search
CPC combination set(s) only.
See application file for complete search history.

(56) References Cited

U.S. PATENT DOCUMENTS

2005/0287666 A1* 12/2005 Kenerson ............. C12N 5/0018
435/372
2008/0299540 A1* 12/2008 Ince ..................... C12N 5/0631
435/4
(Continued)

OTHER PUBLICATIONS

Olivieri et al. "Selenium status, fatty acids, vitamins A and E, and aging: the Nove study" The American Journal of Clinical Nutrition, vol. 60, Issue 4, Oct. 1994. (Year: 1994).*
(Continued)

*Primary Examiner* — Marcia S Noble
*Assistant Examiner* — Lauren K Van Buren
(74) *Attorney, Agent, or Firm* — Wenderoth, Lind & Ponack, L.L.P.

(57) ABSTRACT

The present invention relates to a chemically defined medium for eukaryotic cell culture, comprising water, at least one carbon source, one or more vitamins, one or more salts, one or more growth factors, one or more fatty acids, one or more buffer components, selenium and one or more further trace elements and its use in the culture of cancer stem cells, in particular tumorsphere culture of cancer stem cells.

18 Claims, 3 Drawing Sheets

(51) Int. Cl.
*C12N 5/095* (2010.01)
*C12N 1/00* (2006.01)

(52) U.S. Cl.
CPC ...... *C12N 2500/05* (2013.01); *C12N 2500/10* (2013.01); *C12N 2500/14* (2013.01); *C12N 2500/16* (2013.01); *C12N 2500/22* (2013.01); *C12N 2500/25* (2013.01); *C12N 2500/32* (2013.01); *C12N 2500/36* (2013.01); *C12N 2500/38* (2013.01); *C12N 2500/99* (2013.01); *C12N 2501/11* (2013.01); *C12N 2501/115* (2013.01); *C12N 2501/148* (2013.01); *C12N 2501/15* (2013.01); *C12N 2501/235* (2013.01); *C12N 2501/2306* (2013.01); *C12N 2501/2308* (2013.01); *C12N 2513/00* (2013.01)

(56) References Cited

U.S. PATENT DOCUMENTS

| | | | | |
|---|---|---|---|---|
| 2010/0279412 | A1* | 11/2010 | Kato | C12N 5/0686 435/384 |
| 2011/0178018 | A1* | 7/2011 | Yamashita | A61K 31/4164 514/13.5 |
| 2014/0273205 | A1* | 9/2014 | Price | C12N 5/06 435/348 |
| 2015/0119557 | A1* | 4/2015 | Weng | G01N 33/505 530/389.7 |
| 2016/0022789 | A1 | 1/2016 | Hsieh et al. | |

OTHER PUBLICATIONS

Components of Blood (Khan Academy) (Year: 2016).*
Parr et al. "Trace elements in human milk" IAEA Bulletin, vol. 25, No. 2, none.*
Parr et al. "Trace elements in human milk" IAEA Bulletin, vol. 25, No. 2, none (Year: 2021).*
The Composition of Breast Milk over Time: What's in it? and How does it change? (Year: 2021).*
Bianchi et al. "Dietary Intake of Selenium and its Concentration in Breast Milk" Biological Trace Element Research, vol. 70, 1999 (Year: 1999).*
International Search Report and Written Opinion of the International Searching Authority, dated Apr. 21, 2017 in corresponding International Patent Application No. PCT/EP2017/053666.
"Tumorsphere Culture of Cancer Stem Cells (CSC) with SpheroMax Cancer Stem Cell Medium", Applicant Note D1 of PromoCell GmbH, 2015, regarding PromoCell SpheroMax Cancer Stem Cell Medium; XP055262355; www.promocell.com/fileadmin/promocell/PDF/SpheroMax_Cancer_Stem_Cell_Medium.pdf (2015).

* cited by examiner

CHEMICALLY DEFINED MEDIUM FOR THE CULTURE OF CANCER STEM CELL (CSC) CONTAINING CELL POPULATIONS

FIELD OF THE INVENTION

The present invention relates to chemically defined medium for eukaryotic cell culture, and the use of the medium for the proliferation and/or maintenance of cancer stem cells.

BACKGROUND OF THE INVENTION

All types of stem cells share the hallmarks of self-renewal and the ability to differentiate into various terminally mature cell types. Since these mechanisms are tightly controlled in normal stem cells this potential is progressively lost during the gradual multi-staged differentiation process of stem cells towards terminally differentiated mature cells [1].

In 1863 the pathologist Rudolf Virchow was the first to propose the model of cancer stem cells (CSCs) stating that 'immature cells' represent the origin of cancer [2]. In 1997 Bonnet described a specific subpopulation of CSCs as 'cancer driver cells' in myeloid leukemia [3]. Recently, CSCs have been identified in various cancers including hematopoietic malignancies and a range of solid tumors [4].

In the cancer stem cell model of tumors, CSCs are defined as a small subset of anoikis-resistant malignant cells with the exclusive ability to self-renew and maintain the tumor. They can differentiate into a heterogeneous mass of non-tumorigenic cancer cell types, which usually constitute the majority of the tumor [5]. It is clear in this context that CSCs, despite their malignant phenotype, share common hallmarks of normal stem cells, assigning extraordinary biologic potential to these cells.

CSCs can separate from the primary tumor, travel and spread through the body where they may form secondary tumors (metastases) in distant organs. Metastases may develop quickly or over several years after seemingly successful treatment of the primary tumor. Traditional therapeutic approaches aim to eliminate as much of the tumor mass as possible by means of surgery, irradiation, chemotherapy and biologics. However, accumulating evidence suggests these measures target the more harmless, rapidly dividing cell mass of the tumor and do not eradicate the putative root of the disease—the CSCs.

It is believed that relapse is caused by quiescent CSCs that are able to evade current therapeutic regimens by using protective mechanisms mediated by their stem cell properties. Thus cancer research is now realigned, especially when exploring new clinical strategies to treat malignancies. CSCs are considered to be a new therapeutic target and it is believed that their elimination could lead to permanent remission or even cure. This might be achieved by direct eradication of the CSCs or by specific adaptation of CSC cell division from asymmetric to symmetric leading to elimination of the CSC population by blocking their self-renewal capabilities [5, 6]. For this to be achieved, biologically relevant culture systems are needed allowing for detailed characterization of CSCs.

It is common to all types of stem cells of human origin that characterization and assessment of their functionality for ethical reasons needs to rely on indirect methods.

Today various types of stem cells are well characterized and techniques to reliably identify these cells have been developed. As an example, for pluripotent stem cells the in vivo formation of teratomas in immunocompromised mice or the in vitro generation of embryoid bodies with differentiation into all three germ layers are used as alternative methods of pluripotency testing [7]. Testing for pluripotency marker expression patterns, e.g. Oct-3/4, Nanog, SSEA and Tra antigens is also currently widely accepted as an indirect proof of a pluripotent state (see [8] for review). Thanks to the recent advance of highly defined and optimized culture systems, today scientists are capable of completely defined/ humanized derivation and unrestricted growth of pluripotent stem cells.

In contrast, biologically relevant culture systems for the sustained maintenance of CSCs, as a tool for the exploration of CSC biology and their reliable characterization, are still poorly developed. Therefore, as successfully demonstrated for multiple types of normal stem cells, various approaches have been undertaken to characterize CSCs based on marker detection. These include staining of intra- and extracellular molecules, as well as measuring the activity of certain cellular enzymes, such as aldehyde dehydrogenase (ALDH1) or small molecule transporters like the ABC transport system [9-11]. However, research is hindered by the heterogeneity of CSC in different cancers [5, 12], as well as a lack of specificity, consistency and correlation of established markers with functional CSC features, such as tumorigenesis [5, 13]. Thus, a robust, reliable, and notably holistic, marker based method for CSC detection and characterization has seemed a distant prospect. As a result, currently the greatest obstacle in CSC research is the isolation and purification of sufficient numbers of functional, homogenous CSC populations. These difficulties are exacerbated by a lack of biologically significant in vitro culture systems, which is in sharp contrast to the technical possibilities available for most other types of stem cells.

At present, CSCs can only be defined experimentally by their ability to recapitulate generation of a continuously growing tumor [5]. To date, the most accepted strategies for the analysis of CSCs are generally based on the detection of their basic functional features. These include typical stem cell properties, such as self-renewal and pluripotency, as well as specific hallmarks of cancer, such as serially transferable tumorigenic potential and anoikis-resistance. However, again the lack of a primary model system means that research is forced to rely on indirect readout generated by alternative model systems and tests. The gold standard functional in vivo assay for CSCs is the serial transplantation into orthotopic sites of immunocompromised mice. However, this is laborious and results can be difficult to interpret [5]. One of the most significant in vitro methods selectively exploiting a combination of inherent features of CSCs on an exclusively functional basis is the formation of serially passageable tumorspheres in a 3D suspension culture [5].

Comparable to a malignant tumor, the main cell mass of established cancer cell lines consists of more or less functional terminally differentiated cells with a tissue specificity depending on the type of cancer and tissue they originate of. Therefore, cancer cell lines are widely used in research as broadly accepted, well-defined model systems instead of primary cells for reasons of cost and a constant source of cells avoiding the limitations set by the finite lifespan of normal primary cells.

Indeed, these cell lines contain a small but stable subpopulation of CSC (driver cells) conferring infinite lifespan and proliferation potential to the culture. Thus, today cancer cell lines also represent the most important in vitro model and a well-defined cell source for cancer research, including CSC-targeted approaches [14-19; 27-28].

The two most prominent culture techniques used for these cell lines are:
1) The adherent 2D culture, mostly in standard basal media, e.g. DMEM or DMEM-Ham's F12 Nutrient Mixture supplemented with various amounts of fetal calf serum and eventually additional supplements [16].
2) The second important culture method is the 3D suspension culture as spheres (tumorspheres) employing non-defined but mostly serum-free media based on DMEM-Ham's F12 Nutrient Mixture [18-20].

The adherent 2D culture technique using non-defined media has several drawbacks with regard to CSC:
a) As demonstrated for several types of stem cells, the non-defined nature of these culture media may interfere with stem cell properties and preferentially support differentiation of stem cells, including CSC [21]. The 2D culture in non-defined media is therefore an appropriate culture method to obtain differentiated cells as a primary cell replacement but is an inferior culture method if the CSC subpopulation, which is usually <1% under these conditions, is the target of interest.
b) Non-defined culture media are a potent source of experimental variation. The above mentioned media do not allow for a defined and controlled culture environment. Experimental procedures like cell isolations or drug-screenings to target CSCs may deliver falsified results due to effects of non-defined components of the culture media. In addition, cells may be significantly altered by such culture conditions [22].

The 3D suspension culture technique of tumorspheres was adopted from a method originally developed for the culture of primary neuronal cells as well as brain cancer cells, e.g. glioblastoma as so-called "neurosphere cultures" [23] which could be serially passaged and expanded while maintaining their stem cell pool (self-renewal) and differentiation potential. Thus, this culture method had already proven as a powerful in vitro model for the culture of multipotent neuronal (cancer) cells which helped to speed up exploration of this type of cells significantly.

The media established for these neurosphere cultures worked well in this application and were almost exclusively based on DMEM-Ham's F12 Nutrient Mixture and its variants supplemented with the proprietary B27® supplement (Life Technologies), Insulin, Transferrin, Sodium Selenite, Epidermal Growth Factor (EGF) and basic fibroblast growth factor (bFGF, FGF-2) as a core medium [23]. Eventually, further supplementation e.g. with albumin, hydrocortisone and/or heparin occurred. Since the 3D neurosphere culture technique selectively exploited the inherent biological features of neuronal (cancer) stem cells, e.g. anoikis-resistance and self-renewal capabilities on a merely functional level, it was obvious that this culture method might also prove useful for the culture of CSCs from other types of cancers sharing the same biological properties.

As a result, it was attempted to adopt the neurosphere culture system for other cancer cell cultures as a 3D tumor model system termed "tumorsphere culture" [18, 19]. Since tumorspheres structurally resemble small tumor-like structures and stem cell—as well as tumorigenic properties may be enhanced in this type of culture [20], researchers aimed to use tumorsphere-derived cancer cells instead of cells from 2D standard culture.

However, while the sphere culture method can exploit all afore mentioned technical and biological advantages in the culture of neural (cancer) stem cells, the tumorsphere culture of other cancer cell types still suffers from several shortcomings in this culture system:

1) Not all types of cancer cells cultures can form tumorspheres under these "neurosphere culture conditions" [24].
2) In sharp contrast to neurosphere culture, serial passageability of tumorsphere cultures is often only supported to a limited extend (3-5 serial passages) or even absent [24].

This implies that, as an unwanted effect, the driver cells, i.e. the CSCs, are lost in some way under these culture conditions. Despite these existing limitations, research requests to adopt the unique advantages of tumorsphere culture with regard to its favorable properties as an in vitro tumor model. Thus, scientists are often forced to use cancer cells derived from tumorspheres which have been freshly established from 2D culture or are in very low serial passage. However, cells derived from such degenerating tumorspheres might already be depleted of functional CSCs. In addition, it is very likely that cells in a freshly established tumorsphere culture cannot be compared with cells from a serial passage 10 tumorsphere culture, i.e. the freshly established tumorspheres in low passage would rather exhibit features of the cells from the original serum-containing 2D standard culture while cells from serially passaged tumorspheres in passage 10 will have acquired all the unique features mediated to stem cell populations by this sophisticated culture technique.

Since they trace back to the formulations of the classic neurosphere culture media, the established commercially available and published CSC culture media still share these strong limitations with regard to supporting the culture and maintenance of a broad range of cancer cell types/CSC.

CSCs are a heterogeneous and delicate group of potentially slow-cycling cells [25]. In addition to their stem cell properties, the genetic and metabolic aberrations inherent to cancer cells may be in part responsible for their extended media requirements. Indeed, it is well known that cells undergoing transformation to cancerous cells extensively adapt their metabolism [26].

DMEM-Ham's F12 Nutrient Mixture, as used for established CSC media, was traditionally used as a basis for the development of serum-free culture media and even some chemically defined formulations for several cell types. However, as observed in tumorsphere cultures, DMEM-Ham's F12 Nutrient Mixture cannot reliably fulfil the broadly variable requirements of the heterogeneous group of cancer cells in more defined formulations.

Accordingly it is an object of the present invention to provide a chemically defined cell culture medium for culture of CSC containing cell populations as serially passageable tumorspheres.

SUMMARY OF THE INVENTION

This object is solved by the subject matter of the present invention. The present invention provides a chemically defined medium for eukaryotic cell culture, comprising water, at least one carbon source, one or more vitamins, one or more salts, one or more fatty acids, one or more buffer components, selenium and one or more further trace elements. The chemically defined medium may comprise one or more growth factors. Alternatively, the chemically defined medium may be free of growth factors.

The present inventors have identified the necessary components of a chemically defined culture medium that allows the 3D tumorsphere culture of a broad range of CSC-containing cancer cell lines in a standardized culture environment. The chemically defined medium according to the invention preferably comprises a variety of fatty acids and a variety of trace elements. The chemically defined medium according to the invention enables for continuous proliferation and serial passageability of 3D tumorsphere cultures indicative for CSC self-renewal. Once the fully adapted tumorsphere culture is established, cells can be continuously passaged.

The chemically defined medium allows to exploit the full potential and biological significance of the tumorsphere culture technique as an in vitro tool for maintenance of CSC and as a model of tumor formation.

The present invention further provides the use of the chemically defined medium for culturing of cancer stem cells.

DETAILED DESCRIPTION OF THE INVENTION

Figure 1:
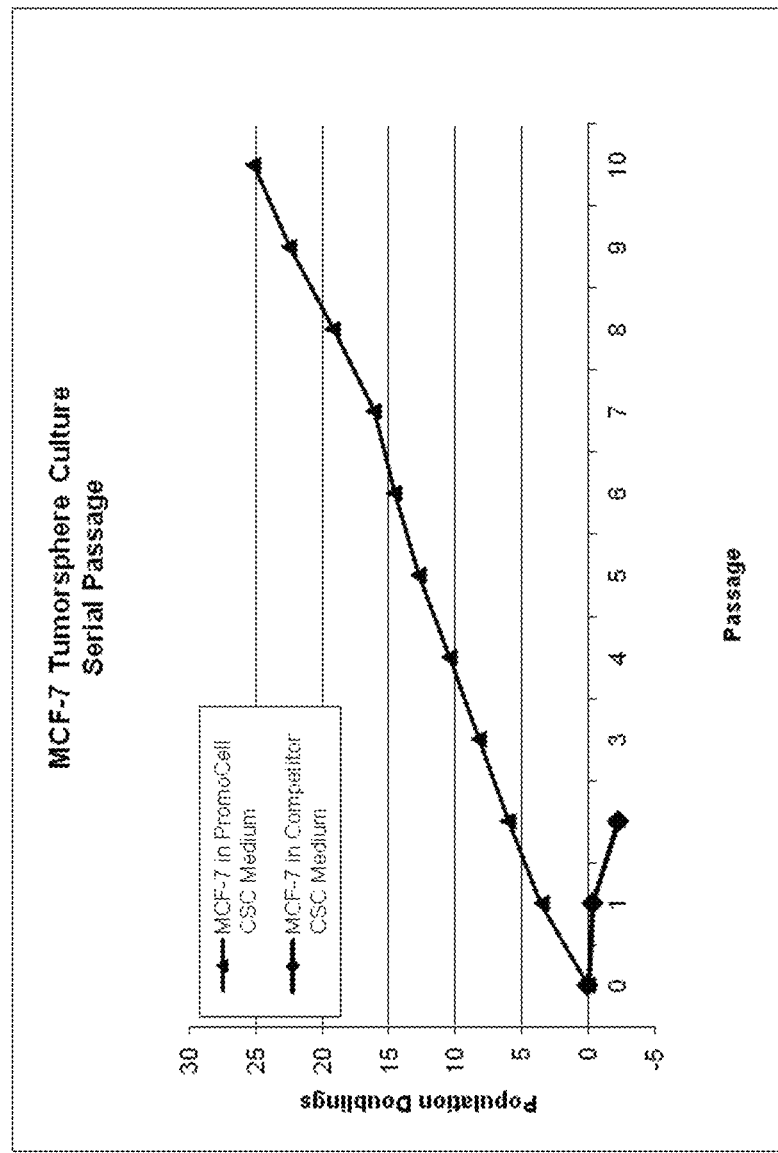
FIG. 1 shows a plot of cumulative population doublings of MCF-7 mammary carcinoma cells during serial passage of 3D tumorsphere culture in CSC Medium 1 (triangles) vs. a comparative CSC medium for tumorsphere culture (diamonds). Forty thousand MCF-7 cells per well (10,000/ml) were plated in triplicate in the respective medium using 6-well suspension culture plates. Serial passage by enzymatic dissociation according to the protocol was performed every 9 days. Tumorsphere formation and proliferation were maintained during the culture, which was discontinued after passage 10 with no sign of growth rate inhibition.

In order to provide a clear and consistent understanding of the specification and claims, and the scope to be given such terms, the following definitions are provided.

The term "ingredient" as used herein refers to any compound, whether of chemical or biological origin, that can be used in cell culture media to maintain or promote the growth or proliferation of cells. The terms "component," "nutrient" and "ingredient" can be used interchangeably and are all meant to refer to such compounds. Typical ingredients that are used in cell culture media include amino acids, salts, metals, sugars, lipids, nucleic acids, hormones, vitamins, fatty acids, proteins and the like. Other ingredients that promote or maintain growth of cells ex vivo can be selected by those of skill in the art, in accordance with the particular need.

The terms "medium", "cell culture medium," "culture medium" and "medium formulation" as used herein refer to a nutritive solution for culturing or growing cells.

"Cell culture" as used herein means cells or tissues that are maintained, cultured or grown in an artificial, in vitro environment. The terms "cultivating" and "culturing" are synonymous.

A "chemically defined medium" as used herein invention is a medium in which all ingredients and concentrations are known. It is in particular "serum-free", i.e. the medium contains no serum (e.g., fetal bovine serum (FBS), human serum, horse serum, goat serum, etc.).

By "culture vessel" it is meant glass containers, plastic containers, or other containers of various sizes that can provide an aseptic environment for growing cells. For example, flasks, single or multiwell plates, single or multi-well dishes, or multiwell microplates can be used.

The terms "feeding" and "medium-change" as used herein refer to replacing the medium in which cells are cultured. The term "passage" and "passaging" as used herein means transferring some or all cells from a previous culture to fresh cell culture medium.

The term "trace element" as used herein refers to a moiety which is present in a cell culture medium in only trace amounts. In the present invention, this term in particular refers to the elements such as Se, Cu, Zn, Fe, Ag, Al, Ba, Cd, Co, Cr, Ge, Se, Br, I, Mn, F, Si, V, Mo, Ni, Rb, Sn or Zr but may also refer to the respective salts comprising these elements in different oxidation states.

The term "salt" or "inorganic salt" as used herein refers to salt of elements that are present in the cell culture medium in more than trace amounts.

"Trace amounts" as used herein, in particular refers to a concentration below 1 mg/L.

The terms "serum-free culture conditions" and "serum-free conditions" refer to cell culture conditions that exclude serum of any type.

In agreement with the definition in the art, according to the invention the term "growth factor" relates to a naturally occurring substance capable of stimulating cellular growth, proliferation, healing, and cellular differentiation, in particular classes of growth factors that carry the term in the name such as epidermal growth factor (EGF), basic fibroblast growth factor (bFGF), or transforming growth factor (TGF), and cytokines such as interleukin 6 (IL-6), interleukin 8 (IL-8).

The present invention provides a chemically defined medium for eukaryotic cell culture, comprising water, at least one carbon source, one or more vitamins, one or more salts, one or more growth factors, one or more fatty acids, one or more buffer components, selenium and one or more further trace elements.

The chemically defined medium according to the invention is a valuable tool for tumorsphere culture. As shown in the examples, the chemically defined medium according to the invention supports serial passage of cancer cell cultures in the form of 3D tumorspheres. Moreover, it is universally applicable for different cancer cell types.

In the formation of a tumor the heterogeneity of events/mutations potentially generating aberrant cells which finally lead to the development of malignancies is reflected in the same genetic and physiologic heterogeneity found in cancer cells when comparing different types of cancers—and even in cells within a single tumor. Established cell lines of all major types of cancers also exhibit variable medium requirements. These cell lines represent broadly accepted in vitro models of these different types of malignancies. The chemically defined medium covers a range of variable metabolic requirements in cancers of different type and tissue origin (table 1).

Furthermore, with the chemically defined medium according to the invention it is possible to grow the cancer cell cultures in regular suspension culture plastic ware. Costly low-attachment plastic ware is not necessary.

According to one embodiment the components of the chemically defined medium are each present in a concentration sufficient to support cancer stem cell proliferation and/or maintenance. The concentration of any ingredient is based on the total volume of the chemically defined medium.

Like every medium for eukaryotic cell culture the chemically defined medium according to the invention contains water, at least one carbon source, one or more vitamins, one or more salts and selenium. These components are also referred to herein as "basic medium ingredients". In the preparation of the chemically defined medium according to the invention the basic medium ingredients may be provided by a basal medium. The term "basal medium" refers to any medium which supporting growth of eukaryotic cells and which by supplement of additional ingredients can be used to form a medium for cell culture according to the invention. The basal medium supplies salts, for example salts of magnesium, calcium, sodium and potassium and optionally salts of trace elements, as well as vitamins, glucose, a buffer system, and essential amino acids. Basal media which can be used in the present invention include but are not limited to Dulbecco's Modified Eagle's Medium (DMEM), Minimal Essential Medium (MEM), Basal Medium Eagle (BME), RPMI 1640, F-10, Ham's F-12, α Minimal Essential Medium (αMEM), Glasgow's Minimal Essential Medium (G-MEM), and Iscove's Modified Dulbecco's Medium.

Accordingly, the chemically defined medium comprises at least one carbon source. The carbon source is preferably a hexose sugar selected from the group of glucose, galactose, mannose and fructose. The sugar is in particular D-glucose. The concentration of the carbon source is preferably in a range from 0.45 g/L to 4.5 g/L.

Also the chemically defined medium comprises one or more salts. The salts are preferably selected from the groups consisting of calcium nitrate tetrahydrate, calcium chloride, magnesium dichloride hexahydrate, magnesium sulfate, magnesium chloride, potassium chloride, potassium nitrate, sodium chloride, sodium phosphate dibasic, sodium phosphate monobasic, sodium bicarbonate and sodium acetate.

The salts are preferably present in a concentration sufficient to support cancer stem cell proliferation and/or maintenance. The salts are for example contained in the medium in following concentrations: Calcium nitrate tetrahydrate in a range from 12 mg/L to 120 mg/L, magnesium dichloride hexahydrate in a range from 9 mg/L to 90 mg/L, magnesium sulfate anhydrous in a range from 4 mg/L to 40 mg/L, potassium chloride in a range from 80 mg/L to 800 mg/L, sodium chloride in a range from 1 g/L to 10 g/L, sodium phosphate dibasic anhydrous in a range from 50 mg/L to 500 mg/L, and sodium phosphate monobasic anhydrous in a range from 4 mg/L to 40 mg/L.

Further basic medium ingredients are the one or more vitamins. The one or more vitamins are preferably selected from D-biotin, D-Ca pantothenate, folic acid, nicotinamide, pyridoxal hydrochloride, pyridoxine hydrochloride, riboflavin, thiamine hydrochloride, vitamin B12, tocopherol acetate, retinol, cholecalciferol, vitamin K1/2 and ascorbic acid, including ascorbic acid phosphate.

The vitamins are present in a concentration sufficient to support cancer stem cell proliferation and/or maintenance. The vitamins are for example contained in the medium in following concentrations: D-Biotin in a range from 0.04 mg/L to 0.4 mg/L, D-Ca pantothenate in a range from 0.3 mg/L to 3 mg/L, folic acid in a range from 0.3 mg/L to 3 mg/L, nicotinamide in a range from 0.3 mg/L to 3 mg/L, pyridoxal hydrochloride in a range from 0.1 mg/L to 1 mg/L, pyridoxine hydrochloride in a range from 0.09 mg/L to 0.9 mg/L, riboflavin in a range from 0.07 mg/L to 0.7 mg/L, thiamine hydrochloride in a range from 0.6 mg/L to 6 mg/L, tocopherol acetate in a range from 8 μg/L to 80 μg/L, vitamin B12 in a range from 0.1 mg/L to 1 mg/L.

The chemically defined medium comprises one or more of the amino acids. The one or more "amino acids" refers to amino acids or their derivatives (e.g., amino acid analogs), as well as their D- and L-forms. The one or more of the amino acids are preferably selected from glycine, L-alanine, L-arginine, L-asparagine L-aspartic acid, L-cysteine, L-cystine, L-glutamic acid, L-histidine, L-proline, L-hydroxyproline, L-isoleucine, L-leucine, L-lysine, L-methionine, L-phenylalanine, L-proline, L-serine, L-threonine, L-tryptophan, L-tyrosine, L-valine. More preferably, the chemically defined medium contains all of these amino acids.

The amino acids are preferably contained the medium in the concentration ranges defined below: Glycine in a range from 2 mg/L to 20 mg/L, L-alanine in a range from 0.5 mg/L to 5 mg/L, L-alanyl-L-glutamine in a range from 230 mg/L to 2.3 g/L, L-arginine monohydrochloride in a range from 13 mg/L to 130 mg/L, L-arginine free base in a range from 15 mg/L to 150 mg/L, L-asparagine monohydrate in a range from 1.2 mg/L to 12 mg/L, L-asparagine anhydrous in a range from 6 mg/L to 60 mg/L, L-aspartic acid 3 mg/L to 30 mg/L, L-cysteine monohydrochloride monohydrate in a range from 1.2 mg/L to 12 mg/L, L-cystine dihydrochloride in a range from 5.5 mg/L to 55 mg/L, L-glutamic acid in a range from 2 mg/L to 20 mg/L, L-histidine monohydrochloride monohydrate in a range from 2.5 mg/L to 25 mg/L, L-hydroxy-L-proline in a range from 3.5 mg/L to 35 mg/L, L-isoleucine in a range from 16 mg/L to 160 mg/L, L-leucine in a range from 7 mg/L to 70 mg/L, L-lysine monohydrochloride in a range from 11 mg/L to 110 mg/L, L-methionine in a range from 1.8 mg/L to 18 mg/L, L-phenylalanine in a range from 7 mg/L to 70 mg/L, L-proline in a range from 6 mg/L to 60 mg/L, L-serine in a range from 4 mg/L to 40 mg/L, L-threonine in a range from 5 mg/L to 50 mg/L, L-tryptophan in a range from 2 mg/L to 20 mg/L, L-tyrosine disodium salt dihydrate in a range from 10 mg/L to 100 mg/L, L-valine in a range from 6 mg/L to 60 mg/L.

According to one embodiment the chemically defined medium further comprises one or more dipeptides selected from the group consisting of L-alanyl-L-glutamine and glycyl-L-glutamine and N-acetyl-L-glutamine.

The one or more vitamins may be selected from D-biotin, D-Ca pantothenate, folic acid, nicotinamide, pyridoxal hydrochloride, pyridoxine hydrochloride, riboflavin, thiamine hydrochloride, tocopherol acetate, vitamin B12.

The trace element selenium is a basic component according to the invention. Preferably, the selenium containing salt is present in a concentration in a range from 40 nM to 400 nM. The chemically defined medium may additionally comprise a standard trace element selected from copper (Cu), iron (Fe), zinc (Zn). The chemically defined medium preferably comprises Fe. The chemically defined medium may for example comprise the standard trace elements Cu and Fe. Alternatively, the chemically defined medium may comprise Fe and Zn. More preferably, the chemically defined medium comprises Cu, Fe and Zn.

The standard trace elements are preferably present in a concentration sufficient to support cancer stem cell proliferation and/or maintenance. Zn is preferably present in chemically defined medium in a range from 80 nM to 800 nM. Cu is preferably present in chemically defined medium in a range from 0.3 nM to 3.0 nM. Fe is preferably present in chemically defined medium in a range from 150 nM to 1.5 µM.

The inventors observed that the presence of at least one further trace element besides the standard trace elements is necessary for the growth of 3D tumorspheres in culture. These one more further trace elements may be selected from the group consisting of aluminum (Al), barium (Ba), bromine (Br), cadmium (Cd), chromium (Cr), cobalt (Co), germanium (Ge), iodine (I), manganese (Mn), nickel (Ni), fluorine (F), molybdenium (Mo), rubidium (Rb), silicon (Si), silver (Ag), tin (Sn), vanadium (V), and zirconium (Zr).

The inventors further identified that the presence of more than one further trace element leads to an improved growth of the 3D tumorspheres. According to one embodiment the chemically defined medium comprises at least three of the further trace elements. Even better results are obtained with at least 5 further trace elements. Preferably it comprises at least five further trace elements, more preferably at least eight further trace elements. The best results for 3D tumorsphere culture were observed with a medium containing all of the following further trace elements: Al, Ba, Br, Cd, Cr, Co, Ge, I, Mn, Ni, F, Mo, Rb, Ag, Si, Sn, V and Zr. Thus, according to one embodiment it comprises the further trace elements Al, Ba, Br, Cd, Cr, Co, Ge, I, Mn, Ni, F, Mo, Rb, Ag, Si, Sn, V and Zr.

The trace elements are preferably introduced into the chemically defined medium as their referring water-soluble salts. For example, aluminium as aluminium chloride, aluminium nitrate or aluminium sulfate. Barium as barium carbonate, barium chloride or barium acetate. Bromine as magnesium bromide, potassium bromide or sodium bromide. Cadmium as cadmium chloride, cadmium nitrate or cadmium sulfate. Chromium as chromium chloride, chromium nitrate or chromium sulfate. Cobalt as cobalt chloride, cobalt nitrate or cobalt sulfate. Copper as copper chloride, copper nitrate or copper sulfate. Fluorine as magnesium fluoride, potassium fluoride or sodium fluoride. Germanium as germanium oxide. Iodine as magnesium iodide, potassium iodide or sodium iodide. Iron as iron chloride, iron citrate, iron nitrate or iron sulfate. Manganese as manganese chloride, manganese nitrate or manganese sulfate. Molybdenium as molybdenium chloride, ammonium molybdate or sodium molybdate. Nickel as nickel chloride, nickel nitrate or nickel sulfate. Rubidium as rubidium chloride, rubidium nitrate or rubidium sulfate. Silver as silver carbonate, silver nitrate or silver sulfate. Selenium as sodium selenite, sodium selenate or selenomethionine. Silicon as potassium silicate or sodium silicate. Tin as tin chloride or tin pyrophosphate. Vanadium as vanadium chloride, vanadyl sulfate or ammonium vanadate. Zinc as zinc chloride, zinc nitrate or zinc sulfate. Zirconium as zirconium oxychloride.

The trace elements are preferably present in the chemically defined medium in a concentration sufficient to support cancer stem cell proliferation and/or maintenance. Preferred concentration ranges of the further trace elements are given below.

Se is preferably present in chemically defined medium in a range from 40 nM to 400 nM. Mn is preferably present in chemically defined medium in a range from 0.1 nM to 1 nM. Si is preferably present in chemically defined medium in a range from 130 nM to 1.3 µM. Mo is preferably present in chemically defined medium in the range from 0.7 nM to 7 nM. V is preferably present in chemically defined medium in a range from 2 nM to 22 nM. Ni is preferably present in chemically defined medium in a range from 0.2 nM to 2 nM. Sn is preferably present in chemically defined medium in a range from 0.1 nM to 1 nM. Al is preferably present in chemically defined medium in a range from 1.5 nM to 15 nM. Ag is preferably present in chemically defined medium in a range from 0.3 nM to 3 nM. Ba is preferably present in chemically defined medium in a range from 1.5 nM to 15 nM. Br is preferably present in chemically defined medium in a range from 0.4 nM to 4 nM. Cd is preferably present in chemically defined medium in a range from 4 nM to 40 nM. Co is preferably present in chemically defined medium in the range from 1 nM to 10 nM. Cr is preferably present in chemically defined medium in the range from 0.5 nM to 5 nM. F is preferably present in chemically defined medium in a range from 12 nM to 120 nM. Ge is preferably present in chemically defined medium in a range from 2 nM to 20 nM. I is preferably present in chemically defined medium in a range from 0.25 nM to 2.5 nM. Rb is preferably present in chemically defined medium in a range from 4 nM to 40 nM. Zr is preferably present in chemically defined medium in a range from 3.5 nM to 35 nM.

Without being bound to theory, the one or more fatty acids should have an effect on tumorsphere culture by facilitating the generation of lipid-associated cell components in fastidiously growing cancer cells. In non-defined media, these compounds are traditionally provided abundantly by the addition of serum.

The one or more fatty acids according to the invention may be selected from saturated and unsaturated fatty acids. The one or more fatty acids may example be selected from the group consisting of arachidonic acid, linoleic acid, linolenic acid, myristic acid, oleic acid, palmitic acid, stearic acid, myristoleic acid, palmitoleic acid, sapienic acid, elaidic acid, vaccenic acid, linoelaidic acid, eicosapentaenoic acid, erucic acid, caprylic acid, capric acid, lauric acid, arachidic acid, behenic acid, lignoceric acid, cerotic acid. With any of these fatty acids in the chemically defined medium 3D tumorsphere culture should be achievable.

The inventors found that good results for in 3D tumorsphere growth are obtained with a chemically defined medium containing the fatty acids arachidonic acid, linolenic acid, oleic acid, myristic acid, palmitic acid, or stearic acid. Thus, according to one embodiment the one or more fatty acids are selected from the group consisting of arachidonic acid, linolenic acid, oleic acid, myristic acid, palmitic acid, stearic acid.

As shown in the examples superior results for 3D tumorsphere culture are obtained with more than one of the fatty acids. According to one embodiment the chemically defined medium comprises at least two of the fatty acids. Preferably, it comprises at least three of the fatty acids, more preferably at least four of the fatty acids. According to one embodiment it comprises arachidonic acid, linoleic acid, linolenic acid, myristic acid, oleic acid, palmitic acid and stearic acid.

The fatty acids are preferably present in the chemically defined medium in a concentration sufficient to support cancer stem cell proliferation and/or maintenance. The total concentration of fatty acids is preferably in a range from 1 to 100 µg/L. Suitable concentrations ranges of the individual fatty acids are given below. Arachidonic acid is preferably present in chemically defined medium in the range from 0.8 µg/L to 8 µg/L, linoleic acid is preferably present in chemically defined medium in a range from 3 µg/L to 30 µg/L, linolenic acid is preferably present in chemically defined medium in a range from 1.2 µg/L to 12 µg/L, myristic acid is preferably present in chemically defined medium in a range from 2.5 µg/L to 25 µg/L, oleic acid is preferably present in chemically defined medium in the range from 3 µg/L to 30 µg/L, palmitic acid is preferably present in chemically defined medium in a range from 2.5 µg/L to 25 µg/L, stearic acid is preferably present in chemically defined medium in a range from 3.8 µg/L to 38 µg/L.

The chemically defined medium according to the invention may in particular contain the further trace elements Al, Ba, Br, Cd, Cr, Co, Ge, I, Mn, Ni, F, Mo, Rb, Si, Ag, Sn, V and Zr and the fatty acids arachidonic acid, linoleic acid, linolenic acid, myristic acid, oleic acid, palmitic acid and stearic acid.

The chemically defined medium according to the invention may comprise one or more agents suitable to reduce shear force in 3D suspension culture. Such agents are for example surfactants such as Pluronic® F-68, Pluronic® 188, and Poloxamer 188 or macromolecules such as polyvinylpyrrolidone (PVP) or polyethyleneglycol (PEG).

According to one embodiment the chemically defined medium according to any of to the invention further comprises at least one surfactant. The surfactant improves the solubility of the fatty acids. The surfactant may further reduce shear force in 3D suspension culture. The surfactant is preferable non-ionic. Nonionic surfactants have the advantage that they allow for solubilization of lipophilic substances in water-based solutions, e.g. cell culture media, providing these lipophilic substances in a bioavailable form to the cells.

The total concentration of surfactants, in particular nonionic surfactants, is preferably in a range from 1 mg/L to 1 g/L, more preferably in a range from 50 mg/L to 500 mg/L, more preferably in a range from 100 to 300 mg/L.

A nonionic surfactant may be selected from the group consisting of polysorbates, Pluronic® F-68, Pluronic® 188, and Poloxamer 188. According to one embodiment the surfactant is Pluronic® F-68. This surfactant is non-toxic to cells and has the advantageous effect of being capable of efficient reduction of shear stress and inhibition of cell attachment to culture vessel surfaces in suspension cultures. Pluronic® F-68 is preferably present in a concentration in a range from 40 to 400 mg/L.

According to one embodiment the surfactant is Tween® 80. This surfactant has the advantageous effect that it is non-toxic to the cells in the applied concentrations and possesses a strong emulsifying/dispersing effect for lipophilic substances in water-based solutions, e.g. cell culture media. Tween® 80 is preferably present in a concentration in a range from 1 to 10 mg/L.

According to one embodiment the chemically defined medium comprises the two nonionic surfactants Tween® 80 and Pluronic® F-68.

According to one embodiment the chemically defined medium may be growth factor free. That is, it does not contain any component acting as a growth factor such as epidermal growth factor (EGF), basic fibroblast growth factor (bFGF), or transforming growth factor (TGF), or a cytokines such as interleukin 6 (IL-6), interleukin 8 (IL-8).

As shown in the examples, the composition of the chemically defined medium according to the invention, in particular due to the presence of the trace elements and fatty acids, is physiologically so well balanced that it sustains the growth of 3D tumorspheres even without any growth factors. The absence of growth factors can be beneficial for specific experimental questions with respect to the tumorsphere culture.

According to an alternative embodiment, the chemically defined medium comprises one or more growth factors. The presence of one or more growth factors in the medium leads to an increased proliferation (see Examples). The one or more growth factors in the chemically defined medium may be selected from the group consisting of epidermal growth factor (EGF), basic fibroblast growth factor (bFGF), transforming growth factor (TGF), interleukin 6 (IL-6), interleukin 8 (IL-8), leukemia inhibitory factor (LIF), According to one embodiment the one or more growth factors of the chemically defined cell culture medium are EGF and bFGF.

According to one embodiment of the chemically defined medium further comprises insulin or an insulin substitute, transferrin or a transferrin substitute, and/or albumin or an albumin substitute. Each of these components is preferably present in the chemically defined medium in a concentration sufficient to support cancer stem cell proliferation and/or maintenance.

The term "albumin substitute" refers to any functional equivalent of albumin. Examples include but are not limited to bovine pituitary extract, plant hydrolysate (e.g., rice/soy hydrolysate), fetuin, egg albumin, human serum albumin (HSA), or another animal-derived albumins, chick extract, bovine embryo extract, AlbuMAX® I, and AlbuMAX® II. Further examples of albumin substitutes are polymers such as polyvinylpyrrolidone (PVP) and polyethylenglycol (PEG).

The term "transferrin substitute" refers to any functional equivalent of transferrin in the supplement. Examples of transferrin substitutes include but are not limited to any iron chelate compound. Iron chelate compounds which may be used include but are not limited to iron chelates of ethylenediaminetetraacetic acid (EDTA), ethylene glycol-bis((3-aminoethyl ether)-N,N,N',N'-tetraacetic acid (EGTA), deferoxamine mesylate, dimercaptopropanol, diethylenetriamine-pentaacetic acid (DPTA), and trans-1,2-diaminocyclohexane-N,N,N',N'-tetraacetic adic (CDTA), aurintricarboxylic acid, as well as a ferric citrate chelate and a ferrous sulfate chelate or Proxyferrin®.

The term "insulin substitute" refers to functional equivalent of insulin. Examples of insulin substitutes include but are not limited to growth factors of the insulin-like growth factors (IGF) group, e.g. IGF-1, IGF-2, LONG®R3IGF-I as well as trace metal insulin mimetics, e.g. $Zn^{2+}$.

Further components of the chemically defined cell culture medium are preferably used in the following concentration ranges: Putrescine dihydrochloride is preferably present in chemically defined medium in a range from 0.015 mg/L to 0.15 mg/L, sodium pyruvate is preferably present in chemically defined medium in a range from 3.14 mg/L to 31.4 mg/L, thioctic acid is preferably present in chemically defined medium in a range from 0.015 mg/L to 0.15 mg/L, thymidine is preferably present in chemically defined medium in a range from 0.025 mg/L to 0.25 mg/L, albumin is preferably present in chemically defined medium in a range from 1.2 g/L to 12 g/L, insulin is preferably present in chemically defined medium in a range from 0.1 mg/L to 1.0 mg/L, transferrin is preferably present in chemically defined medium in the range from 9 mg/L to 90 mg/L, hypoxanthine is preferably present in chemically defined medium in a range from 0.16 mg/L to 1.6 mg/L, para-aminobenzoic acid is preferably present in chemically defined medium in a range from 0.05 mg/L to 0.5 mg/L, myo-inositol is preferably present in chemically defined medium in a range from 7.5 mg/L to 75 mg/L, choline chloride is preferably present in chemically defined medium in a range from 0.7 mg/L to 7.0 mg/L.

Preferably, the chemically defined medium according to the invention comprises albumin, insulin and transferrin.

According to one embodiment the chemically defined medium comprises a buffer element selected from HEPES, inorganic bicarbonate, inorganic phosphate, 3-(N-Morpholino)propanesulfonic acid (MOPS).

According to one embodiment the chemically defined medium contains at least three buffer elements. The three buffer elements are preferably HEPES, inorganic bicarbonate, and inorganic phosphate. It was found that the combination of these buffer components leads to an improved pH stability (in terms of inhibition of media acidification by cellular metabolites) allowing for skipping of media changes between passages while maintaining cell health. This is a significant technical advantage for efficient maintenance of 3D suspension cultures and also facilitates upscaling and automation.

The chemically defined medium according to the invention preferably comprises additionally one or more radical scavengers. Examples of such radical scavengers are glutathione, tocopherol acetate, R-mercaptoethanol, dithiothreitol (DTT), N-acetyl-L-cysteine (NAC), the vitamin L-ascorbic acid or its stable phosphate form.

According to one embodiment a further ingredient of the chemically defined medium is tocopherol acetate, preferably in a concentration sufficient to support cancer stem cell proliferation and/or maintenance. Tocopherol acetate is preferably present in the chemically defined medium in a concentration in a range from 0.0084 mg/L to 0.084 mg/L. Tocopherol acetate as a radical scavenger has the advantage of minimizing harmful lipid peroxidation. According to one embodiment the chemically defined medium contains glutathione in a concentration of 2.14 mg/L to 21.42 mg/L.

According to one embodiment a further ingredient of the chemically defined medium is cholesterol preferably in a concentration sufficient to support cancer stem cell proliferation and/or maintenance. Depending on the growth rate and biosynthetic capabilities of a special type of cell, cholesterol can be a growth limiting nutrient. Especially fastidiously growing cells, e.g. cancer cells, may benefit from cholesterol supplementation allowing for rapid cell mass production by means of efficient cell membrane synthesis. In non-defined, traditional media additional cholesterol is provided by the serum supplementation. Cholesterol is preferably present in the chemically defined medium in a concentration in a range from 0.07 mg/L to 0.75 mg/L.

The chemically defined medium according to the invention preferably does not contain complex non-defined proprietary supplements such as B27®. Moreover, according to one embodiment the chemically defined medium according to the invention does not contain hydrocortisone. It is suggested that hydrocortisone may promote the differentiation of stem cells. According to one embodiment the cell culture medium does not contain heparin, which is an ill-defined animal-derived substance.

A preferred embodiment of the invention is a chemically defined medium comprising the components listed below. Calcium nitrate tetrahydrate, magnesium dichloride hexahydrate, magnesium sulfate anhydrous, potassium chloride, sodium chloride, sodium phosphate dibasic anhydrous, sodium phosphate monobasic anhydrous, Zn, Cu, Fe, Se, Mn, Si, Mo, V, Ni, Sn M, Al, Ag, Ba, Br, Cd, Co, Cr, F, Ge, I, Rb, Zr, glycine, L-alanine, L-alanyl-L-glutamine, L-arginine monohydrochloride, L-arginine free base, L-asparagine monohydrate, L-asparagine anhydrous, L-aspartic acid, L-cysteine monohydrochloride monohydrate, L-cystine dihydrochloride, L-glutamic acid, L-histidine monohydrochloride monohydrate, L-hydroxy-L-proline, L-isoleucine, L-leucine, L-lysine monohydrochloride, L-methionine, L-phenylalanine, L-proline, L-serine, L-threonine, L-tryptophan, L-tyrosine disodium salt dihydrate, L-valine, D-biotin, D-Ca pantothenate, folic acid, nicotinamide, pyridoxal hydrochloride, pyridoxine hydrochloride, riboflavin, thiamine hydrochloride, tocopherol acetate, vitamin B12, arachidonic acid, linoleic acid, linolenic acid, myristic acid, oleic acid, palmitic acid, stearic acid, putrescine dihydrochloride, sodium pyruvate, thioctic acid, thymidine, albumin, insulin, transferrin, hypoxanthine, para-aminobenzoic acid, myo-inositol, choline chloride, HEPES, L-glutathione reduced, D-glucose anhydrous, cholesterol, Tween® 80, Pluronic® F-68, phenol red sodium salt, sodium bicarbonate, water to final volume.

Another preferred embodiment contains the same components but additionally epidermal growth factor, basic fibroblast growth factor.

Preferably components are present in the following concentrations: Calcium nitrate tetrahydrate $6.18 \cdot 10^1$ mg/L, magnesium dichloride hexahydrate $4.18 \cdot 10^1$ mg/L, magnesium sulfate anhydrous $2.09 \cdot 10^1$ mg/L, potassium chloride $4.06 \cdot 10^2$ mg/L, sodium chloride $5.56 \cdot 10^3$ mg/L, sodium phosphate dibasic anhydrous $2.48 \cdot 10^2$ mg/L, sodium phosphate monobasic anhydrous $2.06 \cdot 10^1$ mg/L, Zn $4.13 \cdot 10^2$ nM, Cu 1.56 nM, Fe $7.31 \cdot 10^2$ nM, Se $1.95 \cdot 10^2$ nM, Mn $5.53 \cdot 10^{-1}$ nM, Si $6.4 \cdot 10^2$ nM, Mo 3.48 nM, V $1.08 \cdot 10^1$ nM, Ni $9.64 \cdot 10^{-1}$ nM, Sn $5.70 \cdot 10^{-1}$ nM, Al 7.46 nM, Ag 1.40 nM, Ba 7.99 nM, Br 1.82 nM, Cd $2.11 \cdot 10^1$ nM, Co 5.50 nM, Cr 2.83 nM, F $6.00 \cdot 10^1$ nM, Ge 9.88 nM, 11.33 nM, Rb $1.90 \cdot 10^1$ nM, Zr $1.80 \cdot 10^1$ nM, glycine 9.56 mg/L, L-alanine 2.54 mg/L, L-alanyl-L-glutamine $1.14 \cdot 10^3$ mg/L, L-arginine monohydrochloride $6.31 \cdot 10^1$ mg/L, L-arginine free base $7.60 \cdot 10^1$ mg/L, L-asparagine monohydrate 6.06 mg/L, L-asparagine anhydrous $2.85 \cdot 10^1$ mg/L, L-aspartic acid $1.65 \cdot 10^1$ mg/L, L-cysteine monohydrochloride monohydrate 5.84 mg/L, L-cystine dihydrochloride $2.75 \cdot 10^1$ mg/L, L-glutamic acid $1.04 \cdot 10^1$ mg/L, L-histidine monohydrochloride monohydrate $1.32 \cdot 10^1$ mg/L, L-hydroxy-L-proline $1.85 \cdot 10^1$ mg/L, L-isoleucine $7.94 \cdot 10^1$ mg/L, L-leucine $3.36 \cdot 10^1$ mg/L, L-lysine monohydrochloride $5.61 \cdot 10^1$ mg/L, L-methionine 9.19 mg/L, L-phenylalanine $3.36 \cdot 10^1$ mg/L, L-proline $3.01 \cdot 10^1$ mg/L, L-serine $2.14 \cdot 10^1$ mg/L, L-threonine $2.44 \cdot 10^1$ mg/L, L-tryptophan 9.32 mg/L, L-tyrosine disodium salt dihydrate $5.23 \cdot 10^1$ mg/L, L-valine $3.11 \cdot 10^1$ mg/L, D-biotin $1.88 \cdot 10^{-1}$ mg/L, D-Ca pantothenate 1.42 mg/L, folic acid 1.56 mg/L, nicotinamide 1.58 mg/L, pyridoxal hydrochloride $5.70 \cdot 10^{-1}$ mg/L, pyridoxine hydrochloride $4.41 \cdot 10^{-1}$ mg/L, riboflavin $3.58 \cdot 10^{-1}$ mg/L, thiamine hydrochloride 2.86 mg/L, tocopherol acetate $4.20 \cdot 10^{-2}$ mg/L, vitamin B12 $5.21 \cdot 10^{-1}$ mg/L, arachidonic acid $3.80 \cdot 10^{-3}$ mg/L, linoleic acid $1.62 \cdot 10^{-2}$ mg/L, linolenic acid $6.00 \cdot 10^{-3}$ mg/L, myristic acid $1.30 \cdot 10^{-2}$ mg/L, oleic acid $1.60 \cdot 10^{-2}$ mg/L, palmitic acid $1.20 \cdot 10^{-2}$ mg/L, stearic acid $1.90 \cdot 10^{-2}$ mg/L, putrescine dihydrochloride $7.50 \cdot 10^{-2}$ mg/L, sodium pyruvate $1.57 \cdot 10^1$ mg/L, thioctic acid $7.48 \cdot 10^{-2}$ mg/L, thymidine $1.21 \cdot 10^{-1}$ mg/L, albumin $6.00 \cdot 10^3$ mg/L, insulin $4.97 \cdot 10^{-1}$ mg/L, transferrin $4.45 \cdot 10^1$ mg/L, hypoxanthine $7.98 \cdot 10^{-1}$ mg/L, para-aminobenzoic acid $2.61 \cdot 10^{-1}$ mg/L, myo-inositol $3.84 \cdot 10^1$ mg/L, choline chloride 3.41 mg/L, HEPES $4.56 \cdot 10^3$ mg/L, L-glutathione reduced $1.07 \cdot 10^1$ mg/L, D-glucose anhydrous $2.25 \cdot 10^3$ mg/L, cholesterol $3.74 \cdot 10^{-1}$ mg/L, Tween® 80 3.96 mg/L, Pluronic® F-68 $1.90 \cdot 10^2$ mg/L, phenol red sodium salt 5.93 mg/L, sodium bicarbonate $2.39 \cdot 10^3$ mg/L, water to final volume. The embodiment of the cell culture medium with growth factors contains epidermal growth factor in a concentration of $1.10 \cdot 10^{-2}$ mg/L and the basic fibroblast growth factor in a concentration of $3.60 \cdot 10^{-2}$ mg/L.

The ingredients of the chemically defined medium can be combined by any method known in the art.

The chemically defined medium according to the invention may be prepared according to the following protocol. First, 90% of the final volume cell culture grade water is placed in a mixing vessel. The weighed amounts or appropriate quantities of stock solutions of the referring substance are subsequently added under permanent stirring. Finally, the volume is adjusted and the medium is filter-sterilized using a 0.22 µm filter unit.

The present invention further provides the use of the chemically defined medium for culturing of CSCs, in particular cancer cell cultures including CSCs. Examples of cancer cell lines that may be cultured with the chemically defined medium according to the invention are U-87 MG, MCF-7, HT-29, HT 1080, HepG2, A-549, Panc-1, LNCaP, and A-431.

According to one embodiment the culturing of CSCs is performed as a 3D suspension culture.

The culturing of CSCs may employ the use of a growth factor containing chemically defined cell culture medium and a growth factor free chemically defined cell culture medium.

The invention further relates to a cell culture system comprising cancer cells, in particular including cancer stem cells and the chemically defined medium according to the invention. According to one embodiment of the cell culture system, the cancer cells are primary tumor cells. According to a further embodiment of the cell culture system, the cancer cells are a cancer cell line derived from a tissue selected from brain, breast, colon, connective tissue, liver, lung, pancreas, prostate, and skin. The cancer cell line is in particular selected from U-87 MG, MCF-7, HT-29, HT 1080, HepG2, A-549, Panc-1, LNCaP, and A-431. According to a preferred embodiment the cancer cell line is MCF-7.

The invention also relates to a method of establishing a cancer cell culture comprising the steps:
a) providing a tumor sample previously obtained from the patient,
b) culturing the tumor sample in a chemically defined medium according to the invention, wherein the culturing leads to a proliferation of the tumor cells.

The provision of the tumor sample preferably does not comprise any step of surgery or treatment of the human or animal body. The tumor sample is preferably derived from any of the tissues selected from brain, breast, colon, connective tissue, liver, lung, pancreas, prostate, and skin.

Moreover, the invention relates to a method of proliferating cancer cells in 3D suspension culture comprising the steps:
a) providing a cancer cells in the form of 3D tumorspheres,
b) adding to the 3D tumorspheres to a chemically defined medium according to the invention,
c) culturing the 3D tumorspheres in the chemically defined medium wherein the culturing leads to a proliferation of the tumor cells and/or a growth of the tumorspheres.

According to one embodiment of the method the cancer cells are a cancer cell line derived from a tissue selected from brain, breast, colon, connective tissue, liver, lung, pancreas, prostate, and skin. The cancer cell line is in particular selected from U-87 MG, MCF-7, HT-29, HT 1080, HepG2, A-549, Panc-1, LNCaP, and A-431. According to a preferred embodiment the cancer cell line is MCF-7.

The method may further comprise the passaging of the tumorspheres.

The invention is further defined by the following non-limiting examples.

EXAMPLES

Materials
Cancer Stem Cell Medium
Phosphate Buffered Saline w/o $Ca^{++}/Mg^{++}$ (PBS, PromoCell #C-40232)
Detach-Kit (Trypsin-EDTA and Trypsin Neutralization Solution; PromoCell #C-41210)
6-well Suspension Culture Plates (e.g. Greiner Bio One, #657 185)

Example 1—Preparation of a CSC Medium According to the Invention

First, 90% of the final volume cell culture grade water is placed in a mixing vessel. Except for sodium bicarbonate, the weighed amounts or appropriate quantities of stock solutions of components are subsequently added in the order as defined below under permanent stirring. When everything has gone into solution, the sodium bicarbonate is added and finally the volume is adjusted and the medium is filter-sterilized. The final medium had the following composition: Calcium nitrate tetrahydrate 6.18 $10^1$ mg/L, magnesium dichloride hexahydrate 4.18 $10^1$ mg/L, magnesium sulfate anhydrous 2.09 $10^1$ mg/L, potassium chloride 4.06 $10^2$ mg/L, sodium chloride 5.56 $10^3$ mg/L, sodium phosphate dibasic anhydrous 2.48 $10^2$ mg/L, sodium phosphate monobasic anhydrous 2.06 $10^1$ mg/L, Zn 4.13 $10^2$ nM, Cu 1.56 nM, Fe 7.31 $10^2$ nM, Se 1.95 $10^2$ nM, Mn 5.53 $10^{-1}$ nM, Si 6.4 $10^2$ nM, Mo 3.48 nM, V 1.08 $10^1$ nM, Ni 9.64 $10^{-1}$ nM, Sn 5.70 $10^{-1}$ nM, Al 7.46 nM, Ag 1.40 nM, Ba 7.99 nM, Br 1.82 nM, Cd 2.11 $10^1$ nM, Co 5.50 nM, Cr 2.83 nM, F 6.00 $10^1$ nM, Ge 9.88 nM, 11.33 nM, Rb 1.90 $10^1$ nM, Zr 1.80 $10^1$ nM, glycine 9.56 mg/L, L-alanine 2.54 mg/L, L-alanyl-L-glutamine 1.14 $10^3$ mg/L, L-arginine monohydrochloride 6.31 $10^1$ mg/L, L-arginine free base 7.60 $10^1$ mg/L, L-asparagine monohydrate 6.06 mg/L, L-asparagine anhydrous 2.85 $10^1$ mg/L, L-aspartic acid 1.65 $10^1$ mg/L, L-cysteine monohydrochloride monohydrate 5.84 mg/L, L-cystine dihydrochloride 2.75 $10^1$ mg/L, L-glutamic acid 1.04 $10^1$ mg/L, L-histidine monohydrochloride monohydrate 1.32 $10^1$ mg/L, L-hydroxy-L-proline 1.85 $10^1$ mg/L, L-isoleucine 7.94 $10^1$ mg/L, L-leucine 3.36 $10^1$ mg/L, L-lysine monohydrochloride 5.61 $10^1$ mg/L, L-methionine 9.19 mg/L, L-phenylalanine 3.36 $10^1$ mg/L, L-proline 3.01 $10^1$ mg/L, L-serine 2.14 $10^1$ mg/L, L-threonine 2.44 $10^1$ mg/L, L-tryptophan 9.32 mg/L, L-tyrosine disodium salt dihydrate 5.23 $10^1$ mg/L, L-valine 3.11 $10^1$ mg/L, D-biotin 1.88 $10^{-1}$ mg/L, D-Ca pantothenate 1.42 mg/L, folic acid 1.56 mg/L, nicotinamide 1.58 mg/L, pyridoxal hydrochloride 5.70 $10^{-1}$ mg/L, pyridoxine hydrochloride 4.41 $10^{-1}$ mg/L, riboflavin 3.58 $10^{-1}$ mg/L, thiamine hydrochloride 2.86 mg/L, tocopherol acetate 4.20 $10^{-2}$ mg/L, vitamin B12 5.21 $10^{-1}$ mg/L, arachidonic acid 3.80 $10^{-3}$ mg/L, linoleic acid 1.62 $10^{-2}$ mg/L, linolenic acid 6.00 $10^{-3}$ mg/L, myristic acid 1.30 $10^{-2}$ mg/L, oleic acid 1.60 $10^{-2}$ mg/L, palmitic acid 1.20 $10^{-2}$ mg/L, stearic acid 1.90 $10^{-2}$ mg/L, putrescine dihydrochloride 7.50 $10^{-2}$ mg/L, sodium pyruvate 1.57 $10^1$ mg/L, thioctic acid 7.48 $10^{-2}$ mg/L, thymidine 1.21 $10^{-1}$ mg/L, albumin 6.00 $10^3$ mg/L, insulin 4.97 $10^{-1}$ mg/L, transferrin 4.45 $10^1$ mg/L, hypoxanthine 7.98 $10^{-1}$ mg/L, para-aminobenzoic acid 2.61 $10^{-1}$ mg/L, myo-inositol 3.84 $10^1$ mg/L, choline chloride 3.41 mg/L, epidermal growth factor 1.10 $10^{-2}$ mg/L, basic fibroblast growth factor 3.60 $10^{-2}$ mg/L, HEPES 4.56 $10^3$ mg/L, L-glutathione reduced 1.07 $10^1$ mg/L, D-glucose anhydrous 2.25 $10^3$ mg/L, cholesterol 3.74 $10^{-1}$ mg/L, Tween® 80 3.96 mg/L, Pluronic® F-68 1.90 $10^2$ mg/L, phenol red sodium salt 5.93 mg/L, sodium bicarbonate 2.39 $10^3$ mg/L.

Example 2—Transfer of a Mammary Carcinoma Cell Line from Adherent 2D Culture into 3D Tumorsphere Culture The transfer of the mammary carcinoma cell line MCF-7 from adherent 2D culture in a non-defined standard culture medium into 3D tumorsphere culture in the CSC-culture medium according to example 1 (PromoCell CSC medium) was tested using the protocol below. As a reference, a comparative CSC medium for tumorsphere culture of cancer cell lines was tested concurrently in the same experiment. The comparative CSC medium is Cancer Stem Premium™ produced by Promab Biotechnologies Inc. The exact composition of this medium is not disclosed.

In the protocol both culture media, the CSC Medium 1 and the comparative CSC medium are referred to as CSC medium.

2.1 Harvesting of the Adherent Cells

The cells of a human CSC-containing adherently growing cancer cell line, MCF-7, were detached using standard procedures, i.e. trypsinization with Trypsin-EDTA using the Detach Kit. The cells were 80-90% confluent and in good condition. The cell suspension was centrifuged for 5 minutes at 300×g and the supernatant was aspirated. The cells were resuspended in 5 ml of CSC medium.

2.2. Counting of the Cells

The viable MCF-7 cells were counted using ViaCount™ Reagent and the Muse™ Cell Analyzer (Millipore) and the volume adjusted with the CSC medium to obtain a concentration of 1 million cells/ml.

2.3 Set Up of the Tumorsphere Culture

The MCF-7 cells were seeded in appropriate suspension culture vessels at 10,000 cells/ml, i.e. 40,000 cells in 4 ml of the CSC medium in each well of a 6-well suspension culture plate.

2.4. Allow the Tumorspheres to Grow

The culture was incubated for 9 (8-10) days. Fresh CSC medium was added every 3-4 days with a volume of 50% of the culture volume. No medium was removed.

Example 3—Serial Passage of the 3D Tumorsphere Cultures

The tumorspheres were subjected to serial passages in 3D tumorsphere culture in the CSC medium every 9 (8-10) days according to the protocol below. Passage by means of dissociation of the tumorspheres to single cells and re-plating was performed.

3.1. Collection of the Tumorspheres

The medium containing the tumorspheres was transferred into 15 ml conical tubes using a serological pipette.

3.2. Gravity Sedimentation of the Tumorspheres

The spheres were allowed to settle by gravity sedimentation for 10 minutes at room temperature. The supernatant was aspirated, but approximately 200 µl was left in the conical tube.

3.3. Washing of the Tumorspheres

The sedimentation (step 3.2) was repeated with an equal volume of PBS. Gently aspirate the PBS leaving approximately 200 µl in the conical tube.

3.4. Enzymatic Digestion of the Tumorspheres 1 ml of Trypsin-EDTA was added to the tumorspheres and incubated for 3 minutes at room temperature.

3.5. Break Down of Remaining Cell Aggregates

The spheres were pipetted up and down 10-15 times using a 1000 µl pipette tip to generate a single cell suspension. The cell suspension was aspirated as normal but the pipette tip was tilted slightly at the bottom of the tube when expelling the cells. The shear forces generated facilitated the break-up of any residual cell aggregates. A visual check was performed to confirm that no large cell aggregates remained. Immediately after trituration, twice the volume of Trypsin Neutralization Solution (TNS) was added.

3.6. Determination of the Cell Number and Viability

The volume was brought to 5 ml with fresh CSC Medium and cell number and viability were determined. The cells were spun down for 5 minutes at 300×g. The supernatant was discarded and the cells were resuspended in fresh medium at 1 million cells/ml.

3.7. Plating of the Cells

The cells were reseeded at 10,000 cells/ml in new suspension culture vessels. For this, 6-well plates with 40,000 cells in 4 ml of medium per well were used. For continued serial passage the complete procedure was repeated starting from step 2.4.

3.8. Results

FIG. 1 representatively summarizes the results of the tests performed. The MCF-7 cells transferred from 2D standard culture to the commercially available competitor CSC Medium did generate slowly growing tumorspheres. However, these tumorspheres ceased proliferation and started to decay even before passage 1.

In contrast the tumorspheres cultured in the medium presented here proliferated steadily and underwent 10 serial passages as tumorsphere culture. The test was stopped while the culture showed no sign of exhaustion.

Comparable results were obtained with the HT1080 fibrosarcoma cell line when cultured in the medium described here and the competitor CSC medium. While the tumorsphere culture in the competitor medium ceased after four serial passages the culture in the medium presented here could be passaged for 10 times without any sign of exhaustion (not shown).

Example 4—Determination of the Tumorsphere Formation Efficiency (TFE) of MCF-7 Cells in PromoCell CSC Medium For the MCF-7 cells cultured according to examples 1 and 2, the repeated determination of the tumorsphere formation efficiency (TFE) was performed at different passage numbers during serial passage of the tumorsphere culture. The TFE was determined on serial passage 1, 4 and 9 (P1, P4 and P9) of the MCF-7 tumorsphere culture using the chemically defined medium.

During the passaging process of the tumorsphere culture, single cells are obtained by enzymatic dissociation (see Example 3, step 3.4). At P1, P4 and P9 single cells from tumorsphere dissociation were plated in two 96 well u-bottom suspension culture plates: one single cell per well with 100 µl of the chemically defined medium. After 5-6 days 100 µl fresh medium were added. After 10 days all 192 wells were checked for the presence of tumorspheres and the percentage of all plated cells, which had formed a tumorsphere, was calculated. The percentage of cells capable of tumorsphere formation is the TFE of the cells.

Figure 2:
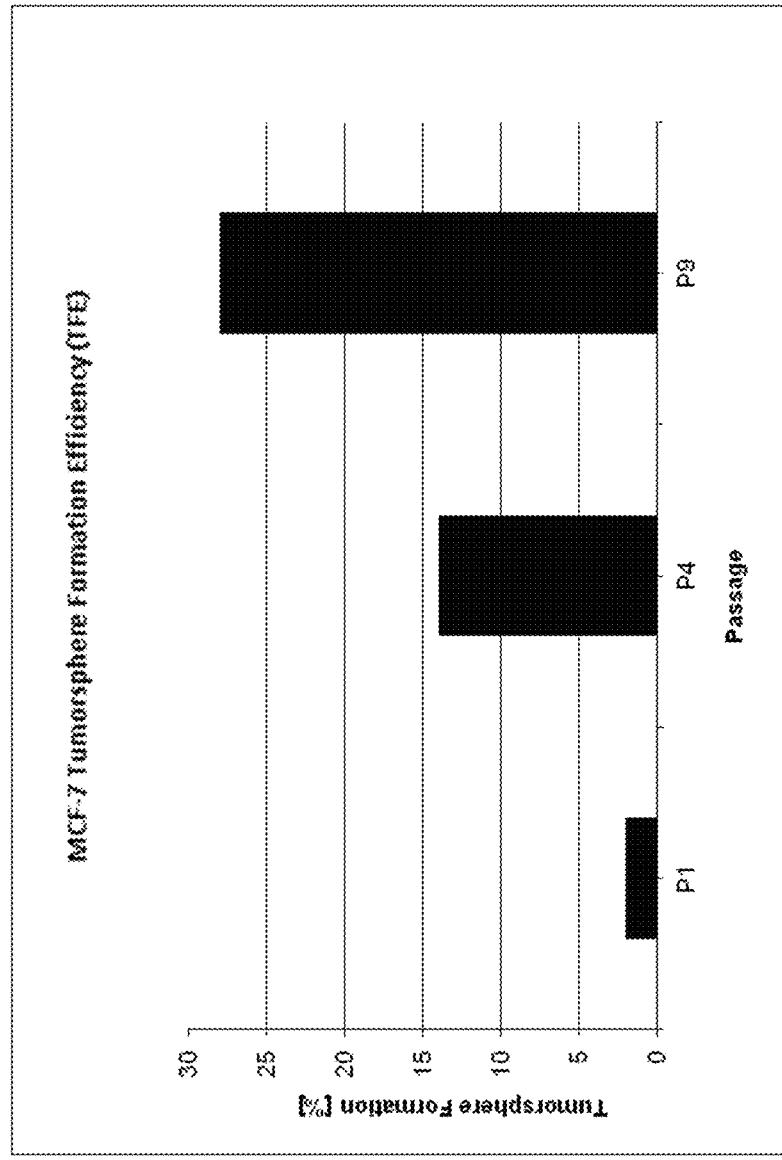
FIG. 2 shows the tumorsphere formation efficiency (TFE) of MCF-7 cells at different passage numbers during serial passage of the tumorsphere culture in the chemically defined medium. MCF-7 cells were plated in 96 well u-bottom suspension culture plates with one single cell per well. After 10 days all wells were checked for the presence of tumorspheres. The percentage of all plated cells, which had formed a tumorsphere, was calculated (TFE in %). The TFE for the MCF-7 cells cultured as tumorspheres in the chemically defined medium was 2% at passage 1 (P1), but increased to 14% in P4 and to 28% in P9 (bars).

The TFE for the MCF-7 cells cultured as tumorspheres in the chemically defined medium was 2% at P1, but increased to 14% in P4 and to 28% in P9 (see FIG. 2). Since only CSC are considered to have the ability of forming a tumorsphere from a single cell, these results suggest that the serial passage of MCF-7 cells as tumorsphere culture in the chemically defined medium significantly augmented the number and percentage of CSC within the culture in a time/passage number dependent manner.

Example 5—3D Tumorsphere Culture of Cancer Cell Lines in the PromoCell CSC Medium In order to verify the broad applicability of the presented medium for the maintenance of cancer cell lines of different origin as 3D tumorsphere culture, the cell lines listed in table 1 standing for the most frequent types of human malignancies were tested for continuous proliferation and serial passageability. All cell lines tested could be expanded as tumorsphere cultures and exhibited continuous proliferation for 10 serial passages. All cultures were terminated at passage 10 without any sign of growth rate inhibition.

TABLE 1

List of cell types tested for serial passage with the PromoCell CSC Medium

| Tissue | Tested Cell Line | Cell Line Origin |
| --- | --- | --- |
| Brain | U-87 MG | Grade IV glioblastoma/astrocytoma of the human brain |
| Breast | MCF-7 | pleural effusion of metastatic human breast adenocarcinoma |
| Colon | HT-29 | human colon adenocarcinoma |
| Connective tissue | HT 1080 | human fibrosarcoma |
| Liver | HepG2 | hepatocellular of the human liver |
| Lung | A-549 | human lung carcinoma |
| Pancreas | Panc-1 | epithelioid carcinoma of the human pancreatic duct |
| Prostate | LNCaP | lymph node metastasis of human prostate adenocarcinoma |
| Skin | A-431 | epidermoid carcinoma of the human skin |

Example 6—3D Tumorsphere Culture of Cancer Cell Lines in the PromoCell CSC Medium 2

The following example shows that the chemically defined medium according to the invention supports 3D tumorsphere growth of cell lines even in the absence of growth factors.

A second cell culture medium was produced, namely PromoCell CSC medium 2 having the same components as PromoCell CSC medium according to Example 1, except that the epidermal growth factor and the basic fibroblast growth factor are not included. The PromoCell CSC medium 2 was produced as described for PromoCell CSC medium in Example 1 omitting the two mentioned growth factors.

The PromoCell the CSC medium 2 was tested in its ability to support tumorsphere growth of two different cancer cell lines. MCF-7 is a cell line and derived from human breast cancer and the cell line HT-29 is a cell line derived from colon cancer.

The two cell lines MCF-7 and HT-29 were cultured according to the protocol of Example 3 using the growth factor free PromoCell CSC medium 2 instead of the growth factor containing PromoCell CSC medium.

Accordingly, the cell lines were subjected to three consecutive (serial) passages with constant passage intervals of 14-16 days for MCF-7 and 10-12 days for HT-29. Both cell lines exhibited robust proliferation with approximately three population doublings per passage.

Figure 3:
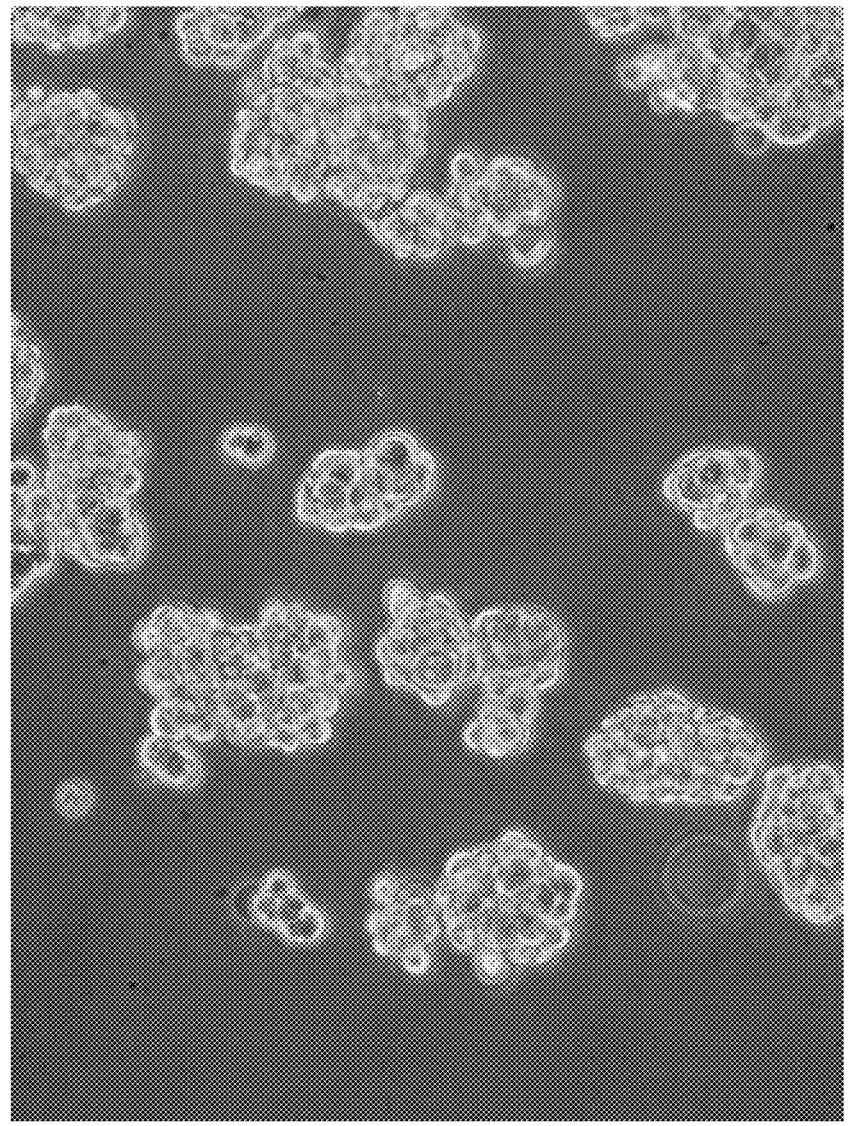
FIG. 3 shows microscopic images of tertiary (passage 3) tumorspheres within 3D culture of MCF-7 cells cultivated in the PromoCell CSC medium 2. The Magnification of the cells is 100 fold.

After the third passage, the cell lines were analyzed. The cultures showed no signs of growth inhibition. Images of the MCF-7 cell culture are shown in FIG. 3 (100× magnification). From FIG. 3 it can be concluded that even in the absence of added growth factors, i.e. EGF and bFGF, the culture is capable of robust formation and growth of tumorspheres in MCF-7 cell culture. In addition, the cells forming the spheres show a uniform and healthy morphology pattern.

In combination with the sustained (despite somewhat decelerated) proliferation rate of the culture, these results indicate that even the growth-factor free variant of the chemically defined medium supports the continued serial 3D tumorsphere culture of human cancer cell lines.

Many modifications and other embodiments of the invention set forth herein will come to mind to the one skilled in the art to which the invention pertains having the benefit of the teachings presented in the foregoing description and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

REFERENCES

1. Sanges, D. and M. P. Cosma, *Reprogramming cell fate to pluripotency: the decision-making signalling pathways*. Int J Dev Biol, 2010. 54(11-12): p. 1575-87.
2. Tu, S. M., *Cancer: a "Stem-cell" disease?* Cancer Cell Int, 2013. 13(1): p. 40.
3. Bonnet, D. and J. E. Dick, *Human acute myeloid leukemia is organized as a hierarchy that originates from a primitive hematopoietic cell*. Nat Med, 1997. 3(7): p. 730-7.
4. Jordan, C. T., *Cancer stem cell biology; from leukemia to solid tumors*. Curr Opin Cell Biol, 2004. 16(6): p. 708-12.
5. Clarke, M. F., et al., *Cancer stem cells—perspectives on current status and future directions: AACR Workshop on cancer stem cells*. Cancer Res, 2006. 66(19): p. 9339-44.
6. Lamb, R., et al., *Antibiotics that target mitochondria effectively eradicate cancer stem cells, across multiple tumor types: treating cancer like an infectious disease*. Oncotarget, 2015. 6(7): p. 4569-84.
7. Sheridan, S. D., V. Surampudi, and R. R. Rao, *Analysis of embryoid bodies derived from human induced pluripotent stem cells as a means to assess pluripotency*. Stem Cells Int, 2012. 2012: p. 738910.
8. Zhao, W., et al., *Embryonic stem cell markers*. Molecules, 2012. 17(6): p. 6196-236.
9. Adil, M., et al., *Aldehyde Dehydrogenase: Cancer and Stem Cells*. 2012.
10. Pearce, D. J., et al., *Characterization of cells with a high aldehyde dehydrogenase activity from cord blood and acute myeloid leukemia samples*. Stem Cells, 2005. 23(6): p. 752-60.
11. Greve, B., et al., *Flow cytometry in cancer stem cell analysis and separation*. Cytometry A, 2012. 81(4): p. 284-93.
12. Stuelten, C. H., et al., *Complex display of putative tumor stem cell markers in the NCI60 tumor cell line panel*. Stem Cells, 2010. 28(4): p. 649-60.
13. Liu, Y., et al., *Lack of correlation of stem cell markers in breast cancer stem cells*. Br J Cancer, 2014. 110(8): p. 2063-71.
14. Kim, H. S., Y. J. Sung, and S. Paik, *Cancer Cell Line Panels Empower Genomics-Based Discovery of Precision Cancer Medicine*. Yonsei Med J, 2015. 56(5): p. 1186-98.
15. Kondo, T., *Stem cell-like cancer cells in cancer cell lines*. Inflammation and Regeneration, 2007. 27(5): p. 506-511.

16. Masters, J. R., *Human cancer cell lines: fact and fantasy.* Nat Rev Mol Cell Biol, 2000. 1(3): p. 233-6.
17. Fillmore, C. M. and C. Kuperwasser, *Human breast cancer cell lines contain stem-like cells that self-renew, give rise to phenotypically diverse progeny and survive chemotherapy.* Breast Cancer Res, 2008. 10(2): p. R25.
18. Min, S. O., et al., *Ideal sphere-forming culture conditions to maintain pluripotency in a hepatocellular carcinoma cell lines.* Cancer Cell Int, 2015. 15: p. 95.
19. Qiu, X., et al., *Characterization of sphere-forming cells with stem-like properties from the small cell lung cancer cell line H446.* Cancer Letters. 323(2): p. 161-170.
20. Grimshaw, M. J., et al., *Mammosphere culture of metastatic breast cancer cells enriches for tumorigenic breast cancer cells.* Breast Cancer Res, 2008. 10(3): p. R52
21. Hurt, E. M., et al., *Identification of vitronectin as an extrinsic inducer of cancer stem cell differentiation and tumor formation.* Stem Cells, 2010. 28(3): p. 390-8.
22. Martin, M. J., et al., *Human embryonic stem cells express an immunogenic nonhuman sialic acid.* Nat Med, 2005. 11(2): p. 228-32.
23. Guerrero-Cazares, H., K. L. Chaichana, and A. Quinones-Hinojosa, *Neurosphere culture and human organotypic model to evaluate brain tumor stem cells.* Methods Mol Biol, 2009. 568: p. 73-83.
24. Calvet, C. Y., F. M. Andre, and L. M. Mir, *The culture of cancer cell lines as tumorspheres does not systematically result in cancer stem cell enrichment.* PLoS One, 2014. 9(2): p. e89644.
25. Moore, N. and S. Lyle, *Quiescent, slow-cycling stem cell populations in cancer: a review of the evidence and discussion of significance.* J Oncol, 2011. 2011.
26. Pecqueur, C., et al., *Targeting metabolism to induce cell death in cancer cells and cancer stem cells.* Int J Cell Biol, 2013. 2013: p. 805975.
27. Akrap, N., et al. *Identification of Distinct Breast Cancer Stem Cell Populations Based on Single-Cell Analyses of Functionally Enriched Stem and Progenitor Pools.* Stem Cell Reports, 2016. 6(1): p. 121-36.
28. Kim, S. and C. M. Alexander. *Tumorsphere assay provides more accurate prediction of in vivo responses to chemotherapeutics.* Biotechnol Lett, 2014. 36(3): p. 481-8.

The invention claimed is:

1. A chemically defined medium for 3D tumorsphere culture, comprising water, at least one carbon source, one or more vitamins, one or more salts, one or more fatty acids, one or more buffer components, and trace elements:
   aluminum (Al), in a concentration in a range of 1.5 nM to 15 nM;
   barium (Ba), in a concentration in a range of 1.5 nM to 15 nM;
   bromine (Br), in a concentration in a range of 0.4 nM to 4 nM;
   cadmium (Cd), in a concentration in a range of 4 nM to 40 nM;
   cobalt (Co), in a concentration in a range of 1 nM to 10 nM;
   chromium (Cr), in a concentration in a range of 0.5 nM to 5 nM;
   germanium (Ge), in a concentration in a range of 2 nM to 20 nM;
   iodine (I), in a concentration in a range of 0.25 nM to 2.5 nM;
   fluorine (F), in a concentration in a range of 12 nM to 120 nM;
   nickel (Ni), in a concentration in a range of 0.2 nM to 2 nM;
   manganese (Mn), in a concentration in a range of 0.1 nM to 1 nM;
   molybdenum (Mo), in a concentration in a range of 0.7 nM to 7 nM;
   rubidium (Rb), in a concentration in a range of 4 nM to 40 nM;
   selenium (Se) in a concentration in a range of 40 nM to 400 nM;
   silver (Ag), in a concentration in a range of 0.3 nM to 3 nM;
   silicon (Si), in a concentration in a range of 130 nM to 1.3 µM;
   tin (Sn), in a concentration in a range of 0.1 nM to 1 nM;
   vanadium (V), in a concentration in a range of 2 nM to 22 nM; and
   zirconium (Zr), in a concentration in a range of 3.5 nM to 35 nM,
   wherein the medium is serum-free.

2. The chemically defined cell culture medium of claim 1, wherein the chemically defined cell culture medium does not comprise any growth factor.

3. The chemically defined cell culture medium of claim 1, comprising one or more growth factors.

4. The chemically defined medium according to claim 3, wherein the one or more growth factors are selected from the group consisting of epidermal growth factor (EGF), basic fibroblast growth factor (bFGF), transforming growth factor (TGF), interleukin 6 (IL-6), interleukin 8 (IL-8), and leukemia inhibitory factor (LIF).

5. The chemically defined medium according to claim 4, wherein the chemically defined cell culture medium comprises EGF and bFGF.

6. The chemically defined medium according to claim 1, wherein the one or more fatty acids are selected from the group consisting of arachidonic acid, linolenic acid, linoleic acid, oleic acid, myristic acid, palmitic acid, and stearic acid, each in a concentration sufficient to support cancer stem cell proliferation and/or maintenance.

7. The chemically defined medium according to claim 6, comprising at least two of the fatty acids.

8. The chemically defined medium according to claim 7, comprising at least three of the fatty acids.

9. The chemically defined medium according to claim 1, further comprising at least one surfactant.

10. The chemically defined medium according to claim 9, comprising two nonionic surfactants polysorbate 80 and Poloxamer 188.

11. The chemically defined medium according to claim 9, wherein the surfactant is a nonionic surfactant selected from the group consisting of polysorbates and Poloxamer 188.

12. The chemically defined medium according to claim 1, further comprising insulin, transferrin, and/or albumin, each in a concentration sufficient to support cancer stem cell proliferation and/or maintenance.

13. The chemically defined medium according to claim 1, wherein the buffer components are selected from the group consisting of HEPES, inorganic bicarbonate, inorganic phosphate, and 3-(N-Morpholino)propanesulfonic acid (MOPS).

14. The chemically defined medium according to claim 1, comprising at least three buffer components.

15. The chemically defined medium according to claim 1, further comprising cholesterol and/or tocopherol acetate.

16. A method of culturing cancer stem cells, comprising culturing cancer stem cells in the chemically defined medium according to claim 1.

17. The method according to claim 16, wherein the culturing of cancer stem cells is performed as 3D suspension culture.

18. A cell culture system, comprising cancer cells, in particular cancer stem cells, and a chemically defined medium according to claim 1.

\* \* \* \* \*